US 6,572,665 B2

United States Patent
Lim et al.

(10) Patent No.: US 6,572,665 B2
(45) Date of Patent: Jun. 3, 2003

(54) COUPLER FOR USE IN OXIDATIVE HAIR DYEING

(75) Inventors: Mu-Ill Lim, Trumbull, CT (US);
Yuh-Guo Pan, Stamford, CT (US);
Margaret Popp, Yonkers, NY (US)

(73) Assignee: Clairol Incorporated, Stamford, CT (US)

(*) Notice: Subject to any disclaimer, the term of this patent is extended or adjusted under 35 U.S.C. 154(b) by 0 days.

(21) Appl. No.: 09/990,749

(22) Filed: Nov. 16, 2001

(65) Prior Publication Data

US 2002/0100126 A1 Aug. 1, 2002

Related U.S. Application Data

(60) Provisional application No. 60/249,857, filed on Nov. 17, 2000.

(51) Int. Cl.$^7$ .................................. A61K 7/13
(52) U.S. Cl. .................. 8/405; 8/405; 8/406; 8/410; 8/412; 8/421; 546/249; 546/329; 546/334
(58) Field of Search .................. 8/405, 406, 410, 8/412, 421; 546/329, 334, 249

(56) References Cited

U.S. PATENT DOCUMENTS 4,065,255 A  12/1977  Andrillon et al. ............ 8/10.2

6,383,230 B1 * 5/2002 Genet et al. .................. 8/405

FOREIGN PATENT DOCUMENTS

EP  0 667 143 B1  10/1996  ............ A61K/7/13
EP  0 634 165 B1  9/1997  ............ A61K/7/13

* cited by examiner

*Primary Examiner*—Yogendra N. Gupta
*Assistant Examiner*—Eisa Elhilo
(74) *Attorney, Agent, or Firm*—Charles J. Zeller

(57) ABSTRACT

Couplers for hair coloring compositions for oxidative dyeing of hair are compounds of the formula (1):

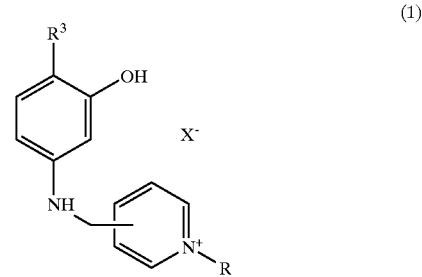

(1)

wherein X is selected from halogen and $R^2SO_4$; $R^3$ is selected from $C_1$ to $C_2$ alkyl or hydroxyethyl; $R^2$ is selected from $C_1$ to $C_{22}$ alkyl and $C_1$ to $C_{22}$ mono and dihydroxyalkyl; and R is selected from of $C_1$ to $C_{16}$ alkyl, $C_1$ to $C_{10}$ hydroxyalkyl, $C_1$ to $C_6$ alkoxyalkyl and benzyl.

12 Claims, No Drawings

COUPLER FOR USE IN OXIDATIVE HAIR DYEING

This application claims benefit of provisional app. No. 60,249,857 filed Nov. 17, 2000.

FIELD OF THE INVENTION

This invention relates to novel couplers for use in hair coloring compositions comprising one or more oxidative hair coloring agents in combination with one or more oxidizing agents. The invention also relates to hair coloring compositions of these novel couplers and to coloring or dyeing of hair using compositions containing these couplers.

BACKGROUND OF THE INVENTION

Coloration of hair is a procedure practiced from antiquity employing a variety of means. In modern times, the most extensively used method employed to color hair is to color hair by an oxidative dyeing process employing hair coloring systems utilizing one or more oxidative hair coloring agents in combination with one or more oxidizing agents.

Most commonly a peroxy oxidizing agent is used in combination with one or more oxidative hair coloring agents, generally small molecules capable of diffusing into hair and comprising one or more primary intermediates and one or more couplers. In this procedure, a peroxide material, such as hydrogen peroxide, is employed to activate the small molecules of primary intermediates so that they react with couplers to form larger sized complunds in the hair shaft to color the hair in a variety of shades and colors.

A wide variety of primary intermediates and couplers have been employed in such oxidative hair coloring systems and compositions. Among the primary intermediates employed there may be mentioned p-phenylenediamine, p-toluenediamine, p-aminophenol, 4-amino-3-methylphenol, and as couplers there may be mentioned resorcinol, 2-methylresorcinol, 3-aminophenol, and 5-amino-2-methylphenol. A majority of the shades have been produced with dyes based on p-phenylenediamine.

For providing an orange coloration to hair 2-methyl-5-aminophenol has been extensively used in combination with p-aminophenol as a primary intermediate. However, the resulting orange color on hair undergoes significant changes on exposure to light or shampooing. U.S. Pat. No. 4,065,255 and EP patent publications EP 634165 A1 and EP 667143 A1 suggest the use of 2-methyl-5-N-hydroxyethylaminophenol, 2-methyl-5-alkylaminophenol and 2-methyl-5-aminophenol as couplers. Therefore, there is a need for new orange couplers for use in oxidative hair dyeing compositions and systems.

BRIEF SUMMARY OF THE INVENTION

This invention provides novel couplers of formula (1):

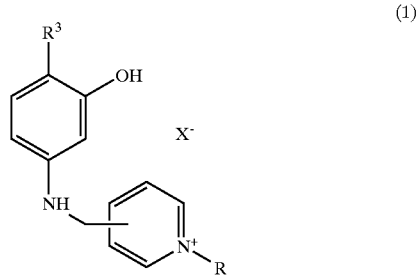

wherein X is selected from halogen or $R^2SO_4$, where the halogen is preferably Cl, Br or I; $R^3$ is selected from $C_1$ to $C_2$ alkyl and hydroxyethyl; $R^2$ is selected from $C_1$ to $C_{22}$ alkyl or $C_1$ to $C_{22}$ mono or dihydroxyalkyl; and R is selected from $C_1$ to $C_{16}$ alkyl, $C_1$ to $C_{10}$ hydroxyalkyl, $C_1$ to $C_6$ alkoxyalkyl and benzyl. These novel couplers are used to provide coloration to hair in which there is good dye uptake by the hair and provides shades or colors which are stable over a relatively long period of time. The novel couplers provide for dyeing of hair that provides color or shades that possess good wash fastness and do not undergo the significant changes on exposure to light or shampooing as experienced with 2-methyl-5-aminophenol.

DETAILED DESCRIPTION OF THE INVENTION

Preferred coupler compounds of this invention are of formula (1)

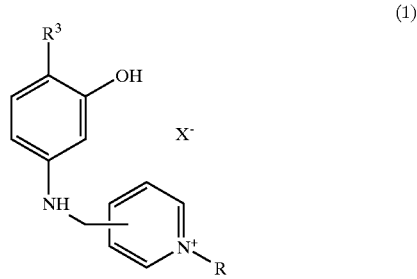

wherein $R^3$ is a methyl group; R is $C_1$ to $C_3$ alkyl, most preferably methyl, $C_1$ to $C_3$ hydroxyalkyl, $C_1$ to $C_4$ alkoxyalkyl and benzyl; and X is selected from Cl, Br, and $R^2SO_4$ where $R^2$ is $C_1$ to $C_3$ alkyl.

Especially preferred couplers of this invention are the following compounds:
3-[(3-hydroxy-4-methyl-phenylamino)-methyl]-1-methyl-pyridinium iodide;
3-[(3-hydroxy-4-methyl-phenylamino)-methyl]-1-benzyl-pyridinium chloride;
3-[(3-hydroxy-4-methyl-phenylamino)-methyl]-1-ethoxyethyl-pyridinium chloride;
3-[(3-hydroxy-4-ethyl-phenylamino)-methyl]-1-methyl-pyridinium chloride;
3-[(3-hydroxy-4-ethyl-phenylamino)-methyl]-1-ethyl-pyridinium chloride;
3-[(3-hydroxy-4-hydroxyethyl-phenylamino)-methyl]-1-methyl-pyridinium chloride;
3-[(3-hydroxy-4-methyl-phenylamino)-methyl]-1-methyl-pyridinium bromide;

3-[(3-hydroxy-4-methyl-phenylamino)-methyl]-1-methyl-pyridinium methyl sulfate; and
3-[(3-hydroxy-4-hydroxyethyl-phenylamino)-methyl]-1-methyl-pyridinium propyl sulfate.

The novel coupler compounds of formula (1) of this invention are readily prepared according to the following reaction sequence:

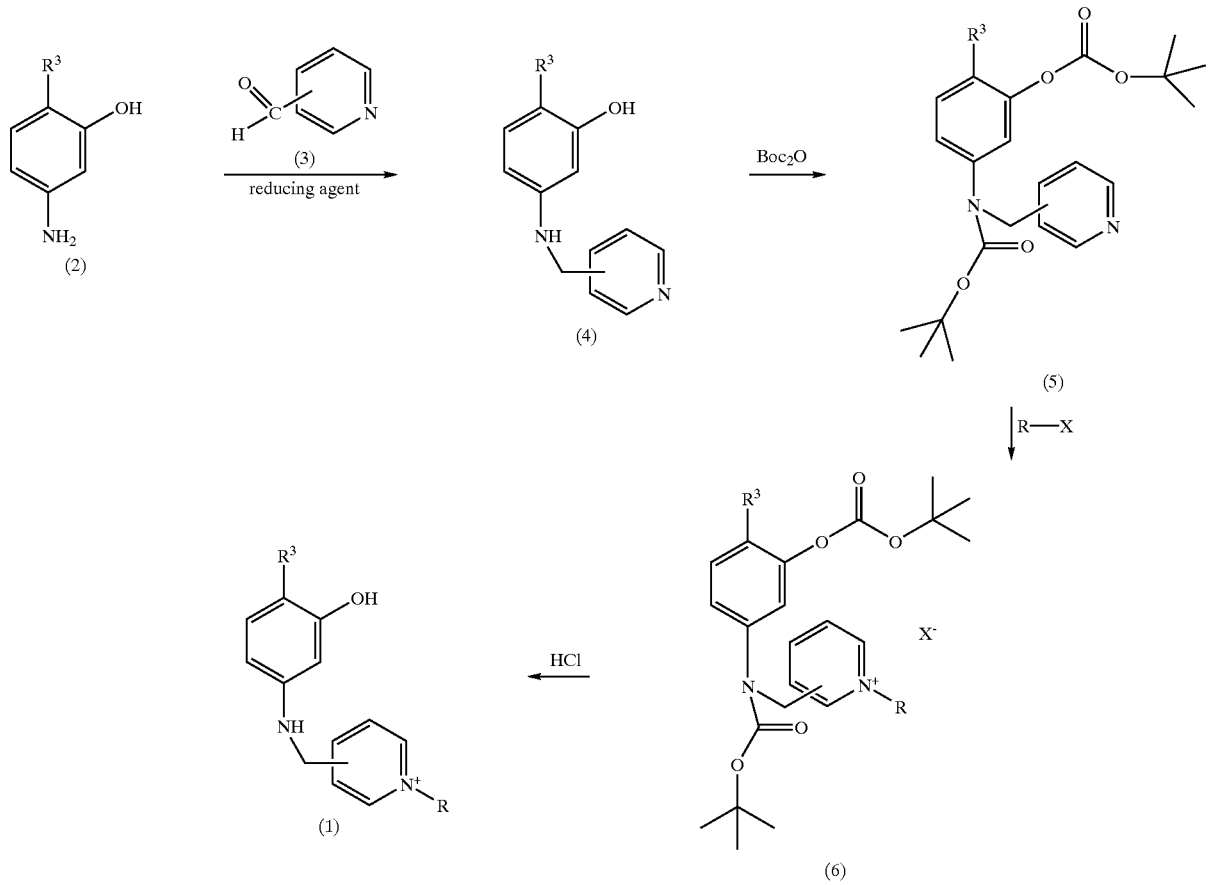

In the reaction sequence reductive amination reaction of an aminophenol of formula (2) with an appropriate pyridine carboxaldehyde of formula (3) in the presence of a suitable reducing agent, such as sodium triacetoxyborohydride or sodium borohydride in 1% acetic acid in 1,2-dichloroethane, produces compound (4). Compound (4) is treated with a suitable blocking or protecting agent, such as di-t-butyl dicarbonate ($Boc_2O$) to produce compound (5) which is reacted with quaternization reagent R-X, such as methyl iodide, to result in the formation of compound (6). Deprotection of compound (6) by treatment with an acid, such as HCl, produces a compound of formula (1) of the invention.

EXAMPLE 1

Synthesis of 3-[(3-hydroxy-4-methyl-phenylamino)-methyl]-1-methyl-pyridinium Chloride 7 (R=Me) (Scheme 1 Below)

A mixture of 5-amino-2-methylphenol 1 (1.23 g, 10 mmol), 3-pyridinecarboxaldehyde 2 (1.18 g, 11 mmol) and sodium triactoxyborohydride (3.18 g, 15 mmol) in 1% AcOH in $ClCH_2CH_2Cl$ (25 mL) was stirred for 18 h at 24° C. and evaporated under reduced pressure. To the solid residue was added water-ice (50 g) and the mixture was stirred for 0.5 h. The resulting precipitate was collected, washed and dried in vacuo to give 2-methyl-5-[(pyridin-3-ylmethyl)amino]-phenol 3 (1.8 g, 84% yield): $^1$HNMR (400 MHz, DMSO-$d_6$) δ 8.82 (s, 1H), 8.52 (s, 1H), 8.40 (d, 1H, J=3.7 Hz), 7.69 (d, 1H, J=7.6 Hz), 7.32 (dd, 1H, J=2.3, 4.9 Hz), 6.68 (d, 1H, J=7.9 Hz), 6.05 (s, 1H), 5.94 (m, 2H), 4.36 (s, 2H), 1.91 (s, 3H); $^{13}$CNMR (400 MHz, DMSO-$d_6$) δ 156.1, 149.1, 148.1, 147.8, 136.3, 135.3, 131.0, 123.8, 111.8, 104.0, 100.0, 44.6, 15.5. A mixture of the compound 3 (0.21 g, 1.0 mmol) and di-tert-butyl dicarbonate ($Boc_2O$) (0.55 g, 2.5 mmol) in anhydrous THF (5 mL) was stirred at room temperature for 18 h and evaporated. To the residue were added ethyl acetate (10 mL) and water (10 mL). The organic layer was separated, washed with water and brine, dried over $MgSO_4$, filtered and evaporated to afford compound 4 as an orange oil (0.35 g, 85% yield): $^1$HNMR (400 MHz, DMSO-$d_6$) δ 8.42 (d, J=4.0 Hz, 1H), 8.37 (s, 1H), 7.58 (d, 1H, J=7.8 Hz), 7.32 (dd, 1H, J=4.9, 7.7 Hz), 7.19 (d, 1H, J=8.1 Hz), 7.02 (m, 2H), 4.84 (s, 2H), 2.05 (s, 3H), 1.46 (s, 9H), 1.36 (s, 9H); $^{13}$CNMR (400 MHz, DMSO-$d_6$) δ 154.0, 151.1, 149.1, 148.9, 148.7, 140.8, 135.3, 134.0, 131.1, 127.6, 124.2, 123.9, 120.2, 83.6, 80.7, 31.7, 28.2, 27.5, 15.4. To a solution of the compound 4 (0.30 g, 0.75 mmol) in anhydrous DMF (3 mL) was added iodomethane 5 (R=Me, 1.5 mmol). The reaction mixture was stirred at room temperature for 18 h and ethyl ether was added. The precipitate was collected, washed with ethyl ether and dried under vacuum to to give compound 6 (R=Me) as a dark yellow solid (0.39 g, 94% yield): $^1$HNMR (400 MHz, DMSO-$d_6$) δ 8.85 (m, 2H), 8.38 (d, 1H, J=8.0 Hz), 8.06 (t, 1H, J=6.8 Hz), 7.24 (d, 1H, J=8.2 Hz), 7.15 (m, 2H), 4.99 (s, 2H), 4.31 (s, 3H), 2.08 (s, 3H), 1.47 (s, 9H), 1.36 (s, 9H); $^{13}$CNMR (400 MHz, DMSO-d$_6$) δ 154.0, 151.2, 149.2, 144.7, 144.2, 143.7, 140.5, 139.2, 131.3, 128.2, 127.8, 124.4, 120.8, 83.7, 81.3, 50.2, 48.4, 28.2, 27.5, 15.4. To compound 6 (R=Me)(379 mg, 0.68 mmol) was added 4M HCl in dioxane (1.7 mL, 6.8 mmol). The reaction mixture was stirred at room temperature for 18 h. Et$_2$O (25 mL) was added and then decanted and dried under vacuum to leave 3-[(3-hydroxy-4-methyl-phenylamino)-methyl]-1-methyl-pyridinium chloride 7 (R=Me, 0.18 g, 72% yield): $^{13}$CNMR (400 MHz, DMSO-d$_6$) δ 155.7, 145.6, 144.1, 143.9, 143.8, 143.7, 141.4, 131.4, 127.6, 114.0, 100.7, 48.3, 44.3, 15.3.

EXAMPLE 2

Synthesis of 3-[(3-hydroxy-4-methyl-phenylamino)-methyl]-1-ethyl-pyridinium Chloride 7 (R=Et) (Scheme 1 Below)

The synthesis of Example 1 was repeated to obtain compound 4. Quarternization of the solution of the compound 4 (0.30 g, 0.75 mmol) with ethyl iodide (1.5 mmol) yielded compound 6 (R=Et) as an orange oil (0.19 g, 72% yield): $^1$HNMR (400 MHz, DMSO-d$_6$) δ 8.96 (d, 1H, J=6.0 Hz), 8.93 (s, 1H), 8.41 (d, 1H, J=8.1 Hz), 8.08 (dd, 1H, J=1.6, 6.2 Hz), 7.24 (d, 1H, J=8.2 Hz), 7.15 (m, 2H), 5.01 (s, 2H), 4.60 (q, 2H, J=7.3 Hz), 2.07 (s, 3H), 1.47 (m, 12H), 1.35 (s, 9H); $^{13}$CNMR (400 MHz, DMSO-d$_6$) δ 153.9, 151.2, 149.2, 145.9, 143.9, 143.6, 143.1, 140.8, 139.6, 131.3, 128.2, 124.3, 120.7, 83.7, 81.3, 56.8, 50.3, 28.1, 27.5, 16.7, 15.4. To compound 6 (379 mg, 0.66 mmol) was added 4M HCl in dioxane (2 mL, 8 mmol). The reaction mixture was stirred at room temperature for 18 h. Et$_2$O (25 mL) was added and then decanted and dried under vacuum to leave 3-[(3-hydroxy-4-methyl-phenylamino)-methyl]-1-ethyl-pyridinium chloride 7 (R=Et; 88% yield): $^{13}$CNMR (400 MHz, DMSO-d$_6$) δ 156.3, 146.4, 144.8, 144.1, 143.5, 143.4, 141.1, 131.2, 127.9, 115.9, 102.6, 56.8, 34.5, 16.6, 15.6. MS calculated for C$_{15}$H$_{20}$N$_2$O (M)$^+$: 244. Found: 244.

Scheme 1
Synthesis of 3-[(3-hydroxy-4-methyl-phenylamino)]-1-methyl or ethyl-pyridinium chloride 7

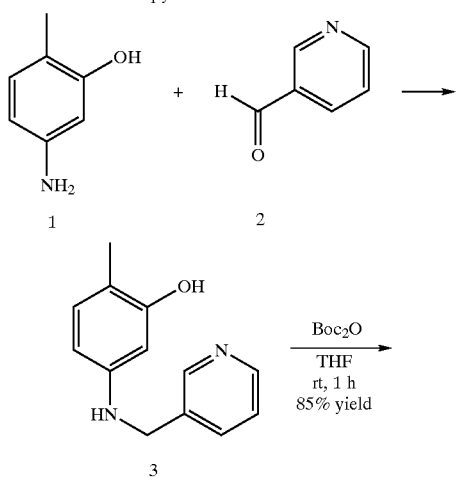

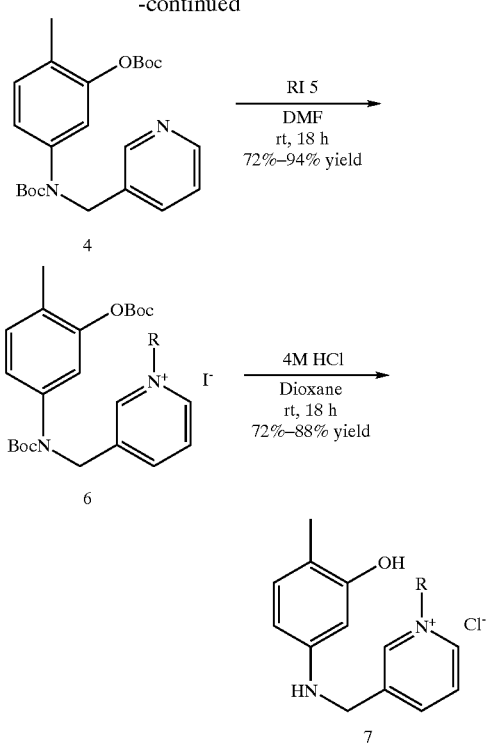

SYNTHESIS EXAMPLE 3–9

By use of the appropriate aminophenol, the appropriate pyridine carboxylaldehyde and the appropriate R-X reagent in the aforedescribed synthesis process the following compounds are prepared:

3-[(3-hydroxy-4-methyl-phenylamino)-methyl]-1-methyl pyridinium iodide;

3-[(3-hydroxy-4-methyl-phenylamino)-methyl]-1-benzyl-pyridinium chloride;

3-[(3-hydroxy-4-methyl-phenylamino)-methyl]-1-ethoxyethyl-pyridinium chloride;

3-[(3-hydroxy-4-ethyl-phenylamino)-methyl]-1-methyl-pyridinium chloride;

3-[(3-hydroxy-4-methyl-phenylamino)-methyl]-1-methyl-pyridinium bromide;

3-[(3-hydroxy-4-methyl-phenylamino)-methyl]-1-methyl-pyridinium methyl sulfate; and 3-[(3-hydroxy-4-hydroxyethyl-phenylamino)-methyl]-1-methyl-pyridinium propyl sulfate.

Hair coloring compositions of this invention can contain the novel couplers of this invention as the sole coupler or can also contain other couplers in combination with primary intermediates.

For hair coloring compositions of this invention, there may be used one or more suitable primary intermediates in combination with the novel couplers of this invention. Suitable primary intermediates include, for example, p-phenylenediamine derivatives such as: benzene-1,4-diamine (commonly known as p-phenylenediamine), 2-methyl-benzene-1,4-diamine, 2-chloro-benzene-1,4-diamine, N-phenyl-benzene-1,4-diamine, N-(2-ethoxyethyl)benzene-1,4-diamine, 2-[(4-aminophenyl)-(2-hydroxy-ethyl)-amino]-ethanol, (commonly known as N,N-bis(2-hydroxyethyl)-p-phenylenediamine) (2,5-diamino-phenyl)-methanol, 1-(2,5-diamino-phenyl)-ethanol, 2-(2,5-diaminophenyl)-ethanol, N-(4-aminophenyl)benzene-1,4-diamine, 2,6-dimethyl-benzene-1,4-diamine, 2-isopropyl-benzene-1,4-diamine, 1-[(4-aminophenyl)amino]-propan-2-ol, 2-propyl-benzene-1,4-diamine, 1,3-bis[(4-aminophenyl)(2-hydroxyethyl)amino] propan-2-ol, $N^4,N^4$, 2-trimethylbenzene-1,4-diamine, 2-methoxy-benzene-1,4-diamine, 1-(2,5-diaminophenyl)ethane-1,2-diol, 2,3-dimethyl-benzene-1,4-diamine, N-(4-amino-3-hydroxy-phenyl)-acetamide, 2,6-diethylbenzene-1,4-diamine, 2,5-dimethylbenzene-1,4-diamine, 2-thien-2-ylbenzene-1,4-diamine, 2-thien-3-ylbenzene-1,4-diamine, 2-pyridin-3-ylbenzene-1,4-diamine, 1,1'-biphenyl-2,5-diamine, 2-(methoxymethyl)benzene-1,4-diamine, 2-(aminomethyl)benzene-1,4-diamine, 2-(2,5-diaminophenoxy)ethanol, N-[2-(2,5-diaminophenoxy)ethyl]-acetamide, N,N-dimethylbenzene-1,4-diamine, N,N-diethylbenzene-1,4-diamine, N,N-dipropylbenzene-1,4-diamine, 2-[(4-aminophenyl)(ethyl)amino]ethanol, 2-[(4-amino-3-methyl-phenyl)-(2-hydroxy-ethyl)-amino]-ethanol, N-(2-methoxyethyl)-benzene-1,4-diamine, 3-[(4-aminophenyl)amino]propan-1-ol, 3-[(4-aminophenyl)-amino]propane-1,2-diol, N-{4-[(4-aminophenyl)amino]butyl}benzene-1,4-diamine, and 2-[2-(2-{2-[(2,5-diaminophenyl)-oxy]ethoxy}ethoxy)ethoxy] benzene-1,4-diamine;

p-aminophenol derivatives such as: 4-amino-phenol (commonly known as p-aminophenol), 4-methylamino-phenol, 4-amino-3-methyl-phenol, 4-amino-2-hydroxymethyl-phenol, 4-amino-2-methyl-phenol, 4-amino-2-[(2-hydroxy-ethylamino)-methyl]-phenol, 4-amino-2-methoxymethyl-phenol, 5-amino-2-hydroxy-benzoic acid, 1-(5-amino-2-hydroxy-phenyl)-ethane-1,2-diol, 4-amino-2-(2-hydroxy-ethyl)-phenol, 4-amino-3-(hydroxymethyl)phenol, 4-amino-3-fluoro-phenol, 4-amino-2-(aminomethyl)-phenol, and 4-amino-2-fluoro-phenol;

o-aminophenol derivatives such as: 2-amino-phenol (commonly known as o-aminophenol), 2,4-diaminophenol, 2-amino-5-methyl-phenol, 2-amino-6-methyl-phenol, N-(4-amino-3-hydroxy-phenyl)-acetamide, and 2-amino-4-methyl-phenol; and heterocyclic derivatives such as: pyrimidine-2,4,5,6-tetramine (commonly known as 2,4,5,6-tetraaminopyridine), 1-methyl-1H-pyrazole-4,5-diamine, 2-(4,5-diamino-1H-pyrazol-1-yl)ethanol, $N^2,N^2$-dimethyl-pyridine-2,5-diamine, 2-[(3-amino-6-methoxypyridin-2-yl)amino]ethanol, 6-methoxy-$N^2$-methyl-pyridine-2,3-diamine, 2,5,6-triaminopyrimidin-4(1H)-one, pyridine-2,5-diamine, 1-isopropyl-1H-pyrazole-4,5-diamine, 1-(4-methylbenzyl)-1H-pyrazole-4,5-diamine, 1-(benzyl)-1H-pyrazole-4,5-diamine and 1-(4-chlorobenzyl)-1H-pyrazole-4,5-diamine.

The couplers of formula (1) of this invention may be used with any suitable coupler(s) in hair coloring compositions or systems of this invention.

Suitable known couplers include, for example:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, 7-amino-4-hydroxy-naphthalene-2-sulfonic acid, 2-isopropyl-5-methyl phenol, 1,2,3,4-tetrahydro-naphthalene-1,5-diol, 2-chloro-benzene-1,3-diol, 4-hydroxy-naphthalene-1-sulfonic acid, benzene-1,2,3-triol, naphthalene-2,3-diol, 5-dichloro-2-methylbenzene-1,3-diol, 4,6-dichlorobenzene-1,3-diol, and 2,3-dihydroxy-[1,4]naphthoquinone;

m-phenylenediamines such as: 2,4-diaminophenol, benzene-1,3-diamine, 2-(2,4-diamino-phenoxy)-ethanol, 2-[(3-amino-phenyl)-(2-hydroxy-ethyl)-amino]-ethanol, 2-mehyl-benzene-1,3-diamine, 2-[[2-(2,4-diamino-phenoxy)-ethyl]-(2-hydroxy-ethyl)-amino]-ethanol, 4-{3-[(2,4-diaminophenyl)oxy]propoxy}benzene-1,3-diamine, 2-(2,4-diamino-phenyl)-ethanol, 2-(3-amino-4-methoxy-phenylamino)-ethanol, 4-(2-amino-ethoxy)-benzene-1,3-diamine, (2,4-diamino-phenoxy)-acetic acid, 2-[2,4-diamino-5-(2-hydroxy-ethoxy)-phenoxy]-ethanol, 4-ethoxy-6-methyl-benzene-1,3-diamine, 2-(2,4-diamino-5-methyl-phenoxy)-ethanol, 4,6-dimethoxy-benzene-1,3-diamine, 2-[3-(2-hydroxy-ethylamino)-2-methyl-phenylamino]-ethanol, 3-(2,4-diamino-phenoxy)-propan-1-ol, N-[3-(dimethylamino)phenyl] urea, 4-methoxy-6-methylbenzene-1,3-diamine, 4-fluoro-6-methylbenzene-1,3-diamine, 2-({3-[(2-hydroxyethyl)amino]-4,6-dimethoxyphenyl}-amino) ethanol, 3-(2,4-diaminophenoxy)-propane-1,2-diol, 2-[2-amino-4-(methylamino)-phenoxy]ethanol, 2-[(5-amino-2-ethoxy-phenyl)-(2-hydroxy-ethyl)-amino]-ethanol, 2-[(3-aminophenyl)amino]ethanol, N-(2-aminoethyl)benzene-1,3-diamine, 4-{[(2,4-diamino-phenyl)oxy]methoxy}-benzene-1,3-diamine, and 2,4-dimethoxybenzene-1,3-diamine;

m-aminophenols such as: 3-amino-phenol, 2-(3-hydroxy-4-methyl-phenylamino)-acetamide, 2-(3-hydroxy-phenylamino)-acetamide, 5-amino-2-methyl-phenol, 5-(2-hydroxy-ethylamino)-2-methyl-phenol, 5-amino-2,4-dichloro-phenol, 3-amino-2-methyl-phenol, 3-amino-2-chloro-6-methyl-phenol, 5-amino-2-(2-hydroxy-ethoxy)-phenol, 2-chloro-5-(2,2,2-trifluoro-ethylamino)-phenol, 5-amino-4-chloro-2-methyl-phenol, 3-cyclopentylamino-phenol, 5-[(2-hydroxyethyl)amino]-4-methoxy-2-methylphenol, 5-amino-4-methoxy-2-methylphenol, 3-(dimethylamino)phenol, 3-(diethylamino)phenol, 5-amino-4-fluoro-2-methylphenol, 5-amino-4-ethoxy-2-methylphenol, 3-amino-2,4-dichloro-phenol, 3-[(2-methoxyethyl)amino]phenol, 3-[(2-hydroxyethyl)amino]phenol, 5-amino-2-ethyl-phenol, 5-amino-2-methoxyphenol, 5-[(3-hydroxypropyl)amino]-2-methylphenol, 3-[(3-hydroxy-2-methylphenyl)-amino] propane-1,2-diol, and 3-[(2-hydroxyethyl)amino]-2-methylphenol; and heterocyclic derivatives such as: 3,4-dihydro-2H-1,4-benzoxazin-6-ol, 4-methyl-2-phenyl-2,4-dihydro-3H-pyrazol-3-one, 6-methoxyquinolin-8-amine, 4-methylpyridine-2,6-diol, 2,3-dihydro-1,4-benzodioxin-5-ol, 1,3-benzodioxol-5-ol, 2-(1,3-benzodioxol-5-ylamino)ethanol, 3,4-dimethylpyridine-2,6-diol, 5-chloropyridine-2,3-diol, 2,6-dimethoxypyridine-3,5-diamine, 1,3-benzodioxol-5-amine, 2-{[3,5-diamino-6-(2-hydroxy-ethoxy)-pyridin-2-yl]oxy}-ethanol, 1H-indole-4-ol, 5-amino-2,6-dimethoxypyridin-3-ol, 1H-indole-5,6-diol, 1H-indole-7-ol, 1H-indole-5-ol, 1H-indole-6-ol, 6-bromo-1,3-benzodioxol-5-ol, 2-aminopyridin-3-ol, pyridine-2,6-diamine, 3-[(3,5-diaminopyridin-2-yl)oxy]propane-1,2-diol, 5-[(3,5-diaminopyridin-2-yl)oxy]pentane-1,3-diol, 1H-indole-2,3-dione, indoline-5,6-diol, 3,5-dimethoxypyridine-2,6-diamine, 6-methoxypyridine-2,3-diamine, and 3,4-dihydro-2H-1,4-benzoxazin-6-amine.

Preferred primary intermediates include:

p-phenylenediamine derivatives such as: 2-methyl-benzene-1,4-diamine, benzene-1,4-diamine, 1-(2,5-diamino-phenyl)-ethanol, 2-(2,5-diamino-phenyl)-ethanol, N-(2-methoxyethyl)benzene-1,4-diamine, 2-[(4-amino-phenyl)-(2-hydroxy-ethyl)-amino]-ethanol, and 1-(2,5-diaminophenyl)ethane-1,2-diol;

p-aminophenol derivatives such as 4-amino-phenol, 4-methylamino-phenol, 4-amino-3-methyl-phenol, 4-amino-2-methoxymethyl-phenol, and 1-(5-amino-2-hydroxy-phenyl)-ethane-1,2-diol;

o-aminophenol derivatives such as: 2-amino-phenol, 2-amino-5-methyl-phenol, 2-amino-6-methyl-phenol, N-(4-amino-3-hydroxy-phenyl)-acetamide, and 2-amino-4-methyl-phenol;

heterocyclic derivatives such as: pyrimidine-2,4,5,6-tetramine, 1-methyl-1H-pyrazole-4,5-diamine, 2-(4,5-diamino-1H-pyrazol-1-yl)ethanol, 1-(4-methylbenzyl)-1H-pyrazole-4,5-diamine, 1-(benzyl)-1H-pyrazole-4,5-diamine and $N^2,N^2$-dimethyl-pyridine-2,5-diamine.

Preferred couplers include:

phenols, resorcinol and naphthol derivatives such as: naphthalene-1,7-diol, benzene-1,3-diol, 4-chlorobenzene-1,3-diol, naphthalen-1-ol, 2-methyl-naphthalen-1-ol, naphthalene-1,5-diol, naphthalene-2,7-diol, benzene-1,4-diol, 2-methyl-benzene-1,3-diol, and 2-isopropyl-5-methylphenol;

m-phenylenediamines such as: benzene-1,3-diamine, 2-(2,4-diamino-phenoxy)-ethanol, 4-{3-[(2,4-diaminophenyl)oxy]propoxy}benzene-1,3-diamine, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1,3-benzodioxol-5-ol, 1,3-benzodioxol-5-amine, 1H-indol-4-ol, 1H-indol-5,6-diol, 1H-indol-7-ol, 1H-indol-5-ol, 1H-indol-6-ol, 1H-indole-2,3-dione, pyridine-2,6-diamine, and 2-aminopyridin-3-ol.

Most preferred primary intermediates include:

p-phenylenediamine derivatives such as: 2-methyl-benzene-1,4-diamine, benzene-1,4-diamine, 2-(2,5-diamino-phenyl)-ethanol, 1-(2,5-diamino-phenyl)-ethanol, and 2-[(4-amino-phenyl)-(2-hydroxy-ethyl)-amino]-ethanol;

p-aminophenol derivatives such as: 4-amino-phenol, 4-methylamino-phenol, 4-amino-3-methyl-phenol, and 1-(5-amino-2-hydroxy-phenyl)-ethane-1,2-diol;

o-aminophenols such as: 2-amino-phenol, 2-amino-5-methyl-phenol, 2-amino-6-methyl-phenol, and N-(4-amino-3-hydroxy-phenyl)-acetamide; and heterocyclic derivatives such as: pyrimidine-2,4,5,6-tetramine, 2-(4,5-diamino-1H-pyrazol-1-yl)ethanol, 1-(4-methylbenzyl)-1H-pyrazole-4,5-diamine, and 1-(benzyl)-1H-pyrazole-4,5-diamine.

Most preferred couplers include:

phenols, resorcinol and naphthol derivatives such as: benzene-1,3-diol, 4-chlorobenzene-1,3-diol, naphthalen-1-ol, 2-methyl-naphthalen-1-ol, and 2-methyl-benzene-1,3-diol;

m-phenylenediamine such as: 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol;

m-aminophenols such as: 3-amino-phenol, 5-amino-2-methyl-phenol, 5-(2-hydroxy-ethylamino)-2-methyl-phenol, and 3-amino-2-methyl-phenol; and heterocyclic derivatives such as: 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

Understandably, the coupler compounds and the primary intermediate compounds, as well as the other dye compounds, in so far as they are bases, can be used as free bases or in the form of their physiologically compatible salts with organic or inorganic acids, such as hydrochloric acid or sulfuric acid, or, in so far as they have aromatic OH groups, in the form of their salts with bases, such as alkali phenolates.

The total amount of the combination of dye precursors (e.g., primary intermediate and coupler compounds) in the hair coloring compositions or systems of this invention is generally from about 0.001 to about 10, preferably from about 0.02 to about 10, and most preferably from about 0.2 to about 6.0 weight percent based on the total weight of the hair coloring composition. The primary intermediate and coupler compounds are generally used in equivalent amounts. However, it is possible to use the primary intermediate compounds in either excess or deficiency, i.e., a molar ratio of primary intermediate to coupler generally ranging from about 5:1 to about 1:5.

The hair coloring compositions of this invention will contain the couplers of this invention in an effective coloring amount, generally in an amount of from about 0.001 to about 6 weight percent by weight of the hair dye composition, preferably from about 0.01 to about 3.5 weight percent. Other couplers, when present, are typically present in an amount such that in aggregate the concentration of couplers in the composition is from about 0.01 to about 6 weight percent. The primary intermediate(s) is present in an effective dyeing concentration generally an amount of from about 0.001 to about 6.0 weight percent by weight of the hair dye composition, preferably from about 0.01 to about 3.5 weight percent. Any suitable carrier or vehicle, generally an aqueous or hydroalcoholic solution, can be employed, preferably an aqueous solution. The carrier or vehicle will generally comprise up to about 40 weight percent.

The hair coloring compositions of this invention may contain one or more cationic, anionic or amphoteric surface active agents, perfumes, antioxidants, sequestering agents, thickening agents, alkalizing or acidifying agents, and other dyeing agents.

The compositions of the present invention are used by admixing them with a suitable oxidant, which reacts with the hair dye precursors to develop the hair dye. Any suitable peroxide providing agent can be employed in the coloring compositions of this invention, particularly hydrogen peroxide ($H_2O_2$) or precursors therefor. Also suitable are urea peroxide, sodium perborate, sodium percarbonate, and melamine peroxide.

Moreover, cosmetic additive ingredients, which are commonly used in compositions for coloring hair, can be used in the hair coloring compositions according to the invention, for example antioxidants, such as ascorbic acid, thioglycolic acid or sodium sulfite, and perfume oils, complex formers, wetting agents, emulsifiers, thickeners and care materials.

The form of the hair coloring compositions according to the invention can be, for example, a solution, especially an aqueous or aqueous-alcoholic solution. However, the form that is particularly preferred is a cream, gel or an emulsion. Its composition is a mixture of the dye ingredients with the conventional cosmetic additive ingredients suitable for the particular preparation.

Conventional cosmetic additive ingredients in solutions, creams, emulsion or gels include, for example:

Solvents

In addition to water, solvents that can be used are lower alkanols (e.g., ethanol, propanol, isopropanol); polyols (e.g., carbitols, propylene glycol, glycerin). Under suitable processing, higher alcohols, such as cetyl alcohol, are suitable organic solvents, provided they are first liquified by melting, typically at low temperature (50 to 80° C.), before incorporation of other, usually lipophilic, materials. See WO 98127941 (section on diluents) incorporated by reference.

Anionic and Nonionic Surfactants

These materials are from the classes of anionic, cationic, amphoteric or nonionic surfactant compounds, such as fatty alcohol sulfates, ethoxylated fatty alcohol sulfates, alkylsulfonates, alkylbenzensulfonates, alkyltrimethylammonium salts, alkylbetaines, ethoxylated fatty alcohols, ethoxylated nonylphenols, fatty acid alkanol amides and ethoxylated fatty acid esters. They are included for various reasons, e.g., to assist in thickening, for forming emulsions, to help in wetting hair during application of the hair dye composition, etc. Suitable materials are alkyl sulfates, ethoxylated alkyl sulfates, alkyl glyceryl ether sulfonates, methyl acyl taurates, acyl isethionates, alkyl ethoxy carboxylates, fatty acid mono- and diethanolamides. Reference is made to WO 98/52523 published Nov. 26, 1998 and incorporated herein by reference.

Thickeners

Suitable thickeners include such as higher fatty alcohols, starches, cellulose derivatives, petrolatum, paraffin oil, fatty acids and anionic and nonionic polymeric thickeners based on polyacrylic and polyurethane polymers. Examples are hydroxyethyl cellulose, hydroxymethylcellulose and other cellulose derivatives, hydrophobically modified anionic polymers and nonionic polymers, particularly such polymers having both hydrophilic and hydrophobic moieties (i.e., amphiphilic polymers). Useful nonionic polymers include polyurethane derivatives such as PEG-150/stearyl alcohol/SDMI copolymer and PEG-150/stearyl alcohol SDMI copolymer. Other useful amphiphilic polymers are disclosed in U.S. Pat. No. 6,010,541 incorporated by reference. Examples of anionic polymers that can be used as thickeners are acrylates copolymer, acrylates/ceteth-20 methacrylates copolymer, acrylates/ceteth-20 itaconate copolymer, and acrylates/beheneth-25 acrylates copolymer. Aculyn® polymers sold by Rohm & Haas, as well as hair care materials, such as cationic resins, lanolin derivatives, cholesterol, pantothenic acids and betaine.

Alkalizing Agents

Suitable materials that are used to increase pH of the hair dye compositions include ammonia, aminomethylpropanol, methylethanolamine, triethanolamine and ethanolamine.

Conditioners

Suitable materials include silicones and silicone derivatives; hydrocarbon oils; monomeric quaternary compounds and quaternized polymers. Monomeric quaternary compounds are typically cationic compounds, but may also include betaines and other amphoteric and zwitterionic materials. Suitable monomeric quaternary compounds include behentrialkonium chloride, behentrimonium chloride, benzalkonium bromide or chloride, benzyl triethyl ammonium chloride, bis-hydroxyethyl tallowmonium chloride, C12–18 dialkyldimonium chloride, cetalkonium chloride, ceteartrimonium bromide and chloride, cetrimonium bromide, chloride and methosulfate, cetylpyridonium chloride, cocamidoproypl ethyldimonium ethosulfate, cocamidopropyl ethosulfate, coco-ethyldimonium ethosulfate, cocotrimonium chloride and ethosulfate, dibehenyl dimonium chloride, dicetyldimonium chloride, dicocodimonium chloride, dilauryl dimonium chloride, disoydimonium chloride, ditallowdimonium chloride, hydrogenated tallow trimonium chloride, hydroxyethyl cetyl dimonium chloride, myristalkonium chloride, olealkonium chloride, soyethomonium ethosulfate, soytrimonium chloride, stearalkonium chloride, and many other compounds. See WO 98/27941 incorporated by reference. Quaternized polymers are typically cationic polymers, but may also include amphoteric and zwitterionic polymers. Useful polymers are exemplified by polyquaternium-4, polyquaternium-6, polyquaternium-7, polyquaternium-8, polyquaternium-9, polyquaternium-10, polyquaternium-22, polyquaternium-32, polyquaternium-39, polyquaternium-44 and polyquaternium-47. Silicones suitable to condition hair are dimethicone, amodimethicone, dimethicone copolyol and dimethiconol. See also WO 99/34770 published Jul. 15, 1999, incorporated by reference, for suitable silicones. Suitable hydrocarbon oils would include mineral oil.

Natural Ingredients

For example, protein derivatives, aloe, camomile and henna extracts.

Other adjuvants include acidulents to lower pH, buffers, chelating agents antioxidants, sequestrants, etc. These classes of materials and other species of materials in the classes referred to above but not specifically identified that are suitable are listed in the International Cosmetics Ingredient Dictionary and Handbook, (Eighth Edition) published by The Cosmetics, Toiletry, and Fragrance Association, incorporated by reference. In particular reference is made to Volume 2, Section 3 (Chemical Classes) and Section 4 (Functions) are useful in identifying a specific adjuvant/excipient to achieve a particular purpose or multipurpose.

The above-mentioned conventional cosmetic ingredients are used in amounts suitable for their purposes. For example the wetting agents and emulsifiers are used in concentrations of from about 0.5 to 30 percent by weight, the thickeners are used in an amount of from about 0.1 to 25 percent by weight and the hair care materials are used in concentrations of from about 0.1 to 5.0 percent by weight.

The hair coloring compositions according to the invention can be weakly acidic, neutral or alkaline according to their composition. The compositions typically have pH values of from 6.8 to 11.5. Their pH can be adjusted in the basic range with ammonia. Also, organic amines can be used for this purpose, including monoethanolamine and triethanolamine, or also inorganic bases, such as sodium hydroxide and potassium hydroxide. Inorganic or organic acids can be used for adjusting the pH in the acid range, for example phosphoric acid, acetic acid, citric acid or tartaric acid.

In order to use the oxidation hair coloring composition for dyeing hair one mixes the above-described hair coloring compositions according to the invention with an oxidizing agent immediately prior to use and applies a sufficient amount of the mixture to the hair, according to the hair abundance, generally from about 60 to 200 grams. Some of the adjuvants listed above (e.g., thickeners, conditoners, etc.) can be provided in the dye composition or the developer, or both, depending on the nature of the ingredients, possible interactions, etc., as is well known in the art.

Typically hydrogen peroxide, or its addition compounds with urea, melamine, sodium borate or sodium carbonate, can be used in the form of a 3 to 12 percent, preferably 6 percent, aqueous solution as the oxidizing agent for developing the hair dye. Oxygen can also be used as the oxidizing agent. If a 6 percent hydrogen peroxide solution is used as oxidizing agent, the weight ratio of hair coloring composition and oxidizing agent is 5:1 to 1:2, but preferably 1:1. The mixture of the oxidizing agent and the dye composition of the invention is allowed to act on the hair for about 10 to about 45 minutes, preferably about 30 minutes, at about 15 to 50° C., the hair is rinsed with water and dried. If necessary, it is washed with a shampoo and eventually after-rinsed with a weak organic acid, such as citric acid or tartaric acid. Subsequently the hair is dried.

The hair coloring composition according to the invention with a compound of formula (1) of this invention as coupler substances permits hair dyeing with outstanding color fastness, especially light fastness, fastness to washing and fastness to rubbing.

In general, a first composition of primary intermediate(s) and coupler(s) is prepared and then, at the time of use, the oxidizing agents, such as $H_2O_2$, is admixed therewith until an essentially homogenous composition is obtained which is applied to the hair to be dyed and permitted to remain in contact with the hair for a dyeing effective amount of time, generally for a period of from about 2 to 45, preferably about 2 to 30, minutes, after which the hair is rinsed, shampooed and dried. Optionally, a separate conditioning product may also be provided. Together the hair dye composition of the present invention comprising the hair dye coupler (1) and the developer comprising the oxidizing agent form a system for dyeing hair. This system may be provided as a kit comprising in a single package separate containers of the hair dye compositions, the developer, the optional conditioner or the hair treatment product, and instructions for use.

EXAMPLE 10

The following composition shown in Table 1 can be used for dyeing Piedmont hair. The dyeing solution is mixed with 100 g 20 volume hydrogen peroxide. The resulting mixture is applied to the hair and permitted to remain in contact with the hair for 30 minutes. The dyed hair is then shampooed and rinsed with water and dried. The ranges of ingredients set out in Table 1 are illustrative of useful concentrations of the recited materials in a hair dye product.

TABLE 1

Composition for Dyeing Hair

| Ingredients | Range (wt %) | Weight (%) |
|---|---|---|
| Cocamidopropyl betaine | 0–25 | 17.00 |
| Monoethanolamine[1] | 0–15 | 2.00 |
| Oleic Acid | 2–22 | 0.75 |
| Citric Acid | 0–3 | 0.10 |
| 28% Ammonium hydroxide[1] | 0–15 | 5.00 |
| Behentrimonium chloride | 1–5 | 0.50 |

TABLE 1-continued

Composition for Dyeing Hair

| Ingredients | Range (wt %) | Weight (%) |
|---|---|---|
| Sodium sulfite | 0–1 | 0.10 |
| EDTA | 0–1 | 0.10 |
| Erythorbic acid | 0–1 | 0.40 |
| Ethoxydiglycol | 1–10 | 3.50 |
| C11-15 Pareth-9 (Tergitol 15-S-9) | 0.5–5 | 1.00 |
| C12-15 Pareth-3 (Neodol 25-3) | 0.25–5 | 0.50 |
| Isopropanol | 2–10 | 4.00 |
| Propylene glycol | 1–12 | 2.00 |
| P-phenylenediamine[2] | 0–5 | 2 mmoles |
| N,N-Bis(hydroxyethyl)-p-phenylene diamine[2] | 0–5 | 2 mmoles |
| 3-Methyl-p-aminophenol[2] | 0–5 | 1 mmoles |
| p-Aminophenol[2] | 0–5 | 5 mmoles |
| Coupler of this invention | 0.5–5 | 5 mmoles |
| 5-Amino-2-Methyl Phenol | 0–5 | 2 mmoles |
| 2,4-Diaminophenoxyethanol | 0–5 | 2 mmoles |
| Water | qs to 100.00 | qs to 100.00 |

[1]In the aggregate, these ingredients are in the range of 2 to 15% by weight.
[2]At least one of these dye precursors is typically present.

Exemplary combinations of hair coloring components employing a novel quaternized pyridinium coupler of formula (1) of this invention are shown in combinations C1 to C126 in Table A. Reading down the columns in Table A, the Xes designate the dye compounds (including the novel couplers of the instant invention) that form illustratively suitable combinations of dyes that can be formulated according to the present invention. For example, in Combination No. C1 in Column 4 of Table A, a quaternized pyridinium coupler formula 1 of this invention, wherein R and $R^3$ are defined hereinbefore, can be combined with p-toluene diamine and 2-amino-phenol. Especially preferred as the quaternized pyridinium couplers in the combinations in Table 1 and C1 to C126 of Table A are:

3-[(3-hydroxy-4-methyl-phenylamino)-methyl]-1-methyl-pyridinium iodide;

3-[(3-hydroxy-4-methyl-phenylamino)-methyl]-1-benzyl-pyridinium chloride;

3-[(3-hydroxy-4-methyl-phenylamino)-methyl]-1-ethoxyethyl-pyridinium chloride;

3-[(3-hydroxy-4-ethyl-phenylamino)-methyl]-1-methyl-pyridinium chloride;

3-[(3-hydroxy-4-ethyl-phenylamino)-methyl]-1-ethyl-pyridinium chloride;

3-[(3-hydroxy-4-hydroxyethyl-phenylamino)-methyl]-1-methyl-pyridinium chloride;

3-[(3-hydroxy-4-methyl-phenylamino)-methyl]-1-methyl-pyridinium bromide;

3-[(3-hydroxy-4-methyl-phenylamino)-methyl]-1-methyl-pyridinium methyl sulfate; and 3-[(3-hydroxy-4-hydroxyethyl-phenylamino)-methyl]-1-methyl-pyridinium propyl sulfate.

TABLE A

DYE COMBINATIONS

| Structure | IUPAC Name | Name | C1 | C2 | C3 | C4 | C5 | C6 | C7 | C8 | C9 | C10 |
|---|---|---|---|---|---|---|---|---|---|---|---|---|
| (structure: $R^3$, OH-substituted benzene linked via HN-CH to N-alkyl pyridinium $X^-$) | 3-Hydroxy-4-alkyl-phenylamino-methyl-1-alkyl-pyridinium halide | 3-Hydroxy-4-alkyl-phenylamino-methyl-1-alkyl-pyridinium halide | X | X | X | X | X | X | X | X | X | X |
| (structure: 2-methyl-1,4-diaminobenzene) | 2-Methyl-benzene-1,4-diamine | p-Toluene-diamine | X | X | X | X | X | X | X | X | X | |
| (structure: 1,4-diaminobenzene) | Benzene-1,4-diamine | p-Phenylene-diamine | | | | | | | | | | X |
| (structure: N,N-bis(2-hydroxyethyl)-p-phenylenediamine) | 2-[(4-Amino-phenyl)-(2-hydroxy-ethyl)-amino]-ethanol | N,N-Bis(2-hydroxyethyl)-p-phenylene-diamine | | | | | | | | | | |
| (structure: 4-aminophenol) | 4-Amino-phenol | p-Aminophenol | | | | | | | | | | |
| (structure: 4-amino-3-methylphenol) | 4-Amino-3-methyl-phenol | 3-Methyl-p-aminophenol | | | | | | | | | | |
| (structure: 2-aminophenol) | 2-Amino-phenol | o-Aminophenol | X | | | | | | | | | X |

TABLE A-continued

| Structure | Name (IUPAC) | Common Name | | | | | | | | | | | | |
|---|---|---|---|---|---|---|---|---|---|---|---|---|---|---|
| Benzene-1,3-diol (HO-C6H4-OH) | Benzene-1,3-diol | Resorcinol | X | | | | | | | | | | | |
| 2-Methyl-benzene-1,3-diol | 2-Methyl-benzene-1,3-diol | 2-Methyl-resorcinol | | X | | | | | | | | | | |
| Naphthalen-1-ol | Naphthalen-1-ol | 1-Naphthol | | | X | | | | | | | | | |
| 2-Methyl-naphthalen-1-ol | 2-Methyl-naphthalen-1-ol | 2-Methyl-1-naphthol | | | | X | | | | | | | | |
| 2-(2,4-Diamino-phenoxy)-ethanol | 2-(2,4-Diamino-phenoxy)-ethanol | 2,4-Diamino-phenoxyethanol | | | | | X | | | | | | | |
| Benzene-1,3-diamine | Benzene-1,3-diamine | m-Phenylenediamine | | | | | | X | | | | | | |
| 3-Amino-phenol | 3-Amino-phenol | m-Aminophenol | | | | | | | X | | | | | |
| 5-Amino-2-methyl-phenol | 5-Amino-2-methyl-phenol | 2-Hydroxy-4-aminotoluene | | | | | | | | X | | | | |
| 2-(4,5-Diamino-pyrazol-1-yl)-ethanol | 2-(4,5-Diamino-pyrazol-1-yl)-ethanol | 1-Hydroxyethyl-4,5-diamino-pyrazole | | | | | | | | | | | | | |

| | DYE COMBINATIONS | | | | | | | | | | | | | |
|---|---|---|---|---|---|---|---|---|---|---|---|---|---|---|
| Structure | | C11 | C12 | C13 | C14 | C15 | C16 | C17 | C18 | C19 | C20 | C21 | C22 | C23 | C24 |

TABLE A-continued

| Structure | 1 | 2 | 3 | 4 | 5 | 6 | 7 | 8 | 9 | 10 | 11 | 12 | 13 |
|---|---|---|---|---|---|---|---|---|---|---|---|---|---|
| 4-(R³)-3-hydroxyphenyl-NH-CH₂-pyridinium (X⁻, N⁺-R) | X | X | X | X | X | X | X | X | X | X | X | X | X |
| 2-methyl-1,4-phenylenediamine | | | | | | | | X | X | X | X | X | X |
| 1,4-phenylenediamine | X | X | X | X | X | X | X | X | | | | | |
| 4-{N,N-bis(2-hydroxyethyl)amino}aniline | | | | | | | | | | | | | |
| 4-aminophenol | | | | | | | | X | X | X | X | X | X |
| 4-hydroxy-2-methylaniline | | | | | | | | | | | | | |
| 2-aminophenol | | | | | | | | | | X | | | |
| resorcinol | | X | | | | | | | | X | | | |

TABLE A-continued
| Structure | C25 | C26 | C27 | C28 | C29 | C30 | C31 | C32 | C33 | C34 | C35 | C36 | C37 | C38 |
|---|---|---|---|---|---|---|---|---|---|---|---|---|---|---|
| 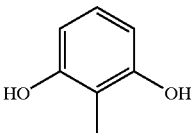 | X | | | | | | | X | | | | | | |
| 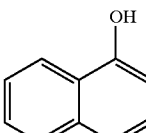 | | X | | | | | | | X | | | | | |
| 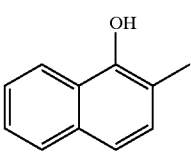 | | | X | | | | | | | X | | | | |
| 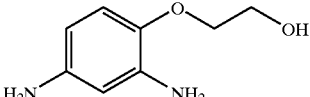 | | | | X | | | | | | | | | X | |
| 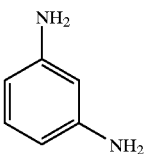 | | | | | X | | | | | | | | | |
| 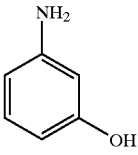 | | | | | | X | | | | | | | | |
| 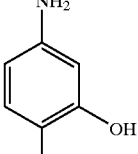 | | | | | | | X | | | | | | | |
| 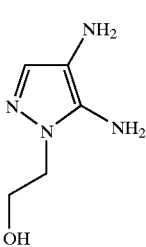 | | | | | | | | | | | | | | |
DYE COMBINATIONS TABLE A-continued

| Structure | | | | | | | | | | | | | |
|---|---|---|---|---|---|---|---|---|---|---|---|---|---|
| R³-phenyl(OH)-NH-CH₂-pyridinium-R, X⁻ | X | X | X | X | X | X | X | X | X | X | X | X | X |
| 2-methyl-1,4-diaminobenzene | X | X | X | | | | | | | | X | X | |
| 1,4-diaminobenzene | | | | X | X | X | X | X | X | X | X | X | |
| 4-amino-N,N-bis(2-hydroxyethyl)aniline | | | | | | | | | | | | X | X |
| 4-aminophenol | X | X | X | X | X | X | X | X | X | X | X | X | |
| 4-amino-3-methylphenol | | | | | | | | | | | | | |
| 2-aminophenol | | | | X | | | | | | | X | | |
| resorcinol | | | | X | | | | | | | X | | |

TABLE A-continued
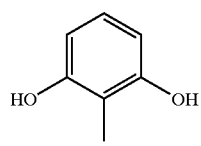                                    X
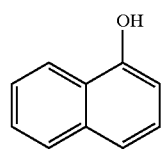                                                X
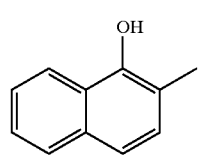                                                X
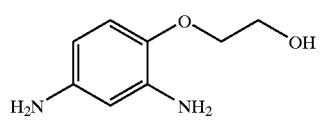                                           X
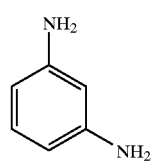                    X                                 X
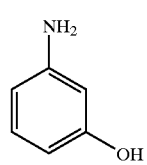                         X                                 X
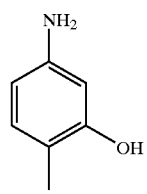                              X                                 X
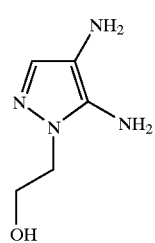
| | DYE COMBINATIONS | | | | | | | | | | | | |
|---|---|---|---|---|---|---|---|---|---|---|---|---|---|
| Structure | C39 | C40 | C41 | C42 | C43 | C44 | C45 | C46 | C47 | C48 | C49 | C50 | C51 | C52 |

TABLE A-continued
| Structure | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 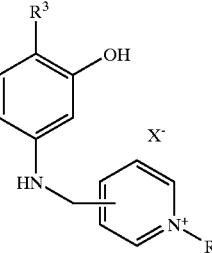 | X | X | X | X | X | X | X | X | X | X | X | X | X | X |
| 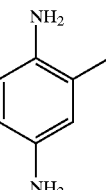 | X | X | X | X | X | X | X | | | | | | | |
| 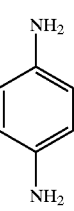 | | | | | | | | X | X | X | X | X | X | X |
| 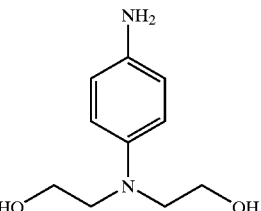 | X | X | X | X | X | X | X | X | X | X | X | X | X | X |
| 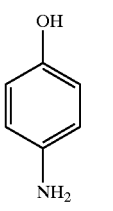 | | | | | | | | | | | | | | |
| 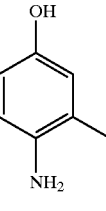 | | | | | | | | | | | | | | |
| 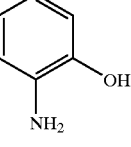 | | | | | | | | | | X | | | | |
| 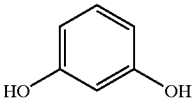 | | | | | | | | | | | X | | | |

TABLE A-continued
| Structure | C53 | C54 | C55 | C56 | C57 | C58 | C59 | C60 | C61 | C62 | C63 | C64 | C65 | C66 |
|---|---|---|---|---|---|---|---|---|---|---|---|---|---|---|
| 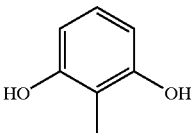 2-methylresorcinol | X | | | | | | | | X | | | | | |
| 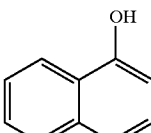 1-naphthol | | X | | | | | | | | X | | | | |
| 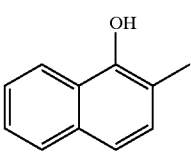 2-methyl-1-naphthol | | | X | | | | | | | | X | | | |
| 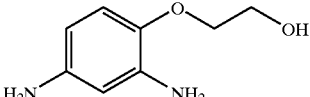 2,4-diamino-phenoxyethanol | | | | X | | | | | | | | X | | |
| 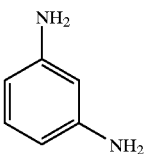 m-phenylenediamine | | | | | X | | | | | | | | | |
| 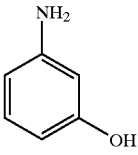 3-aminophenol | | | | | | X | | | | | | | | |
| 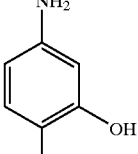 5-amino-2-methylphenol | | | | | | | X | | | | | | | |
| 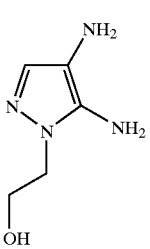 4,5-diamino-1-(2-hydroxyethyl)pyrazole | | | | | | | | | | | | | | |
DYE COMBINATIONS TABLE A-continued

| Structure | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| 5-($R^3$, OH-phenyl)aminomethyl-1-R-pyridinium $X^-$ | X | X | X | X | X | X | X | X | X | X | X | X | X | X |
| 2-methyl-1,4-phenylenediamine | | | | | | | | | | | | | | |
| 1,4-phenylenediamine | X | X | | | | | | | | | | | | |
| 4-[bis(2-hydroxyethyl)amino]aniline | X | X | | | | | | | | | | | | |
| 4-aminophenol | x | X | X | X | X | X | X | X | X | | | | | |
| 4-hydroxy-2-methylaniline | | | | | | | | | | | | x | X | X |
| 2-aminophenol | | | x | | | | | | | | | x | | |
| resorcinol | | | | x | | | | | | | | | x | |

TABLE A-continued
| Structure | C67 | C68 | C69 | C70 | C71 | C72 | C73 | C74 | C75 | C76 | C77 | C78 | C79 | C80 |
|---|---|---|---|---|---|---|---|---|---|---|---|---|---|---|
| 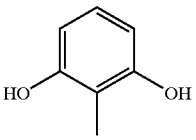 |  |  |  |  | x |  |  |  |  |  |  |  |  | x |
| 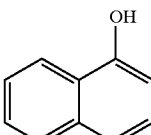 |  |  |  |  |  |  |  | x |  |  |  |  |  |  |
| 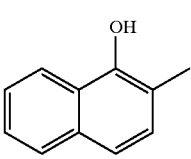 |  |  |  |  |  |  |  |  | x |  |  |  |  |  |
| 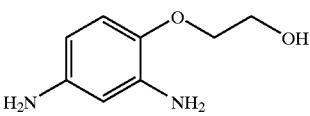 |  |  |  |  |  |  |  |  |  | x |  |  |  |  |
| 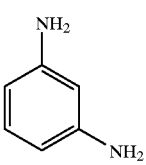 |  | X |  |  |  |  |  |  |  |  | x |  |  |  |
| 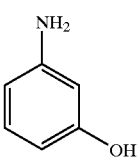 |  | X |  |  |  |  |  |  |  |  | x |  |  |  |
| 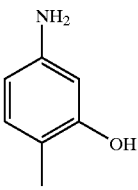 |  |  |  | X |  |  |  |  |  |  |  | x |  |  |
| 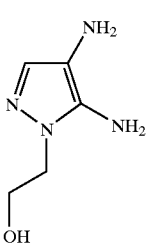 |  |  |  |  |  |  |  |  |  |  |  |  |  |  |
DYE COMBINATIONS TABLE A-continued
| Structure | | | | | | | | | | | | | |
|---|---|---|---|---|---|---|---|---|---|---|---|---|---|
| 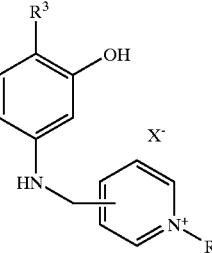 | x | x | x | x | x | x | x | x | x | x | x | x | x |
| 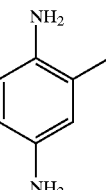 | | | | | | | | | | | | | |
| 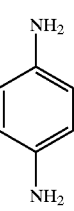 | | | | | | | | | | | | | |
| 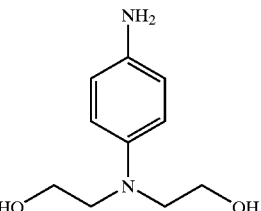 | | | | | | x | x | x | x | x | x | x | x |
| 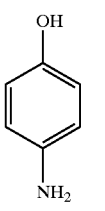 | | | | | | x | x | x | x | x | x | x | x |
| 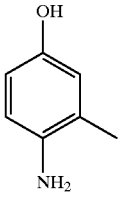 | x | x | x | x | x | x | | | | | | | |
| 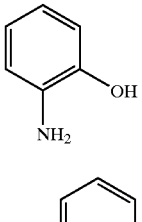 | | | | | | | | | x | | | | |
| 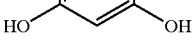 | | | | | | | | | x | | | | |

TABLE A-continued
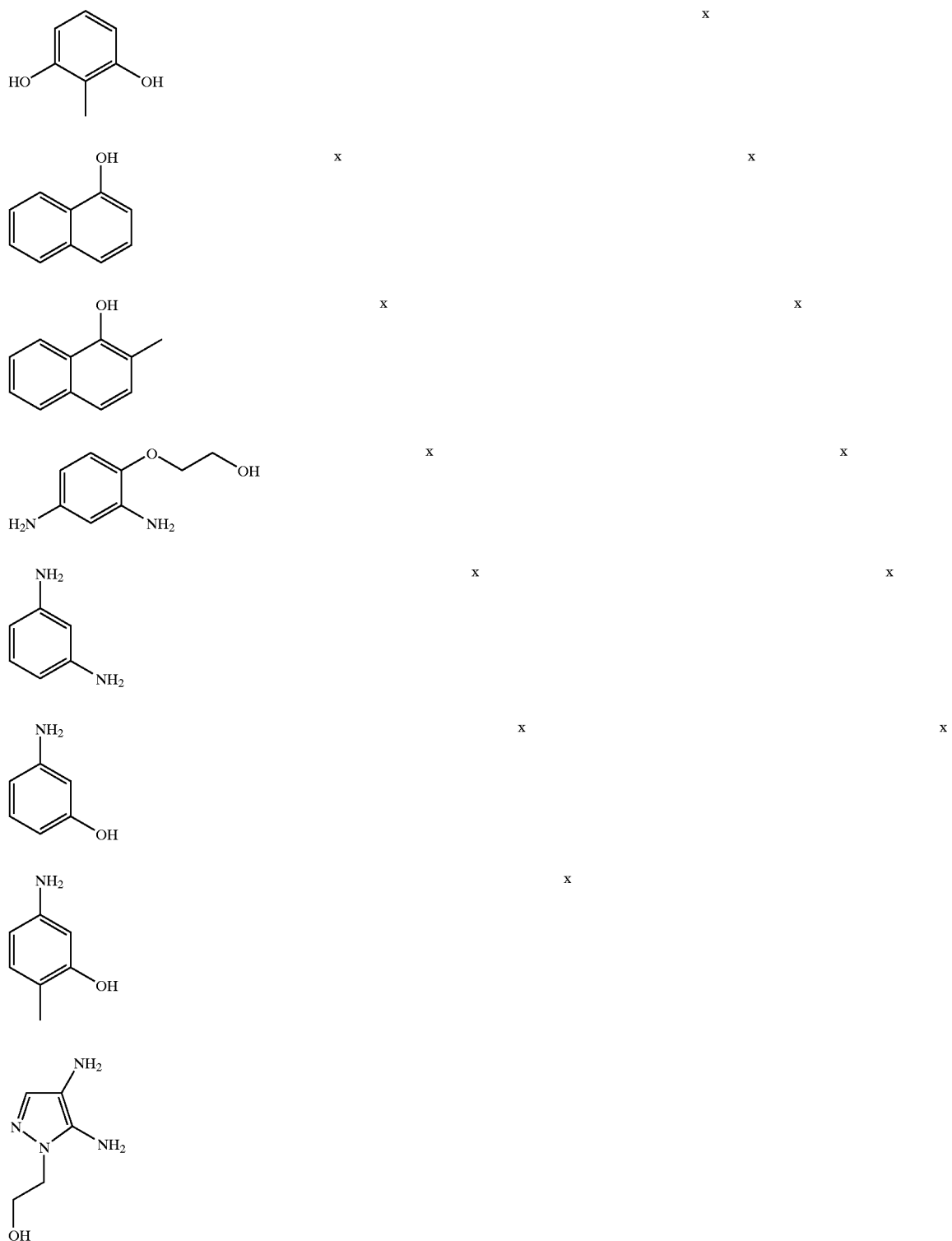
| Structure | DYE COMBINATIONS | | | | | | | | | | | | | |
|---|---|---|---|---|---|---|---|---|---|---|---|---|---|
| | C81 | C82 | C83 | C84 | C85 | C86 | C87 | C88 | C89 | C90 | C91 | C92 | C93 | C94 |

TABLE A-continued
| | | | | | | | | | | | | | | | |
|---|---|---|---|---|---|---|---|---|---|---|---|---|---|---|---|
| 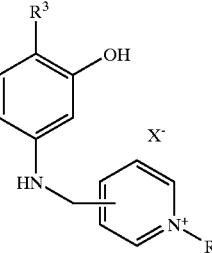 | X | X | X | X | X | X | X | X | X | X | X | X | X | X | X |
| 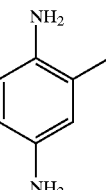 | | | | | | | | | | | X | X | X | X | |
| 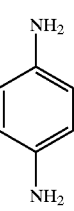 | | | | | | | | | | | | | | | |
| 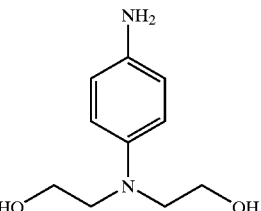 | X | X | X | X | X | X | X | X | X | X | | | | | |
| 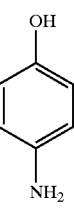 | X | | | | | | | | | | | | | | |
| 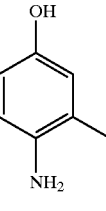 | X | X | X | X | X | X | X | X | X | | | | | | |
| 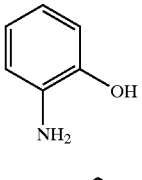 | X | | | | | | | X | | | | | | | |
| 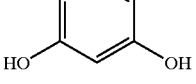 | X | | | | | | | X | | | | | | | |

TABLE A-continued

| Structure | C95 | C96 | C97 | C98 | C99 | C100 | C101 | C102 | C103 | C104 | C105 | C106 | C107 | C108 |
|---|---|---|---|---|---|---|---|---|---|---|---|---|---|---|
| 2-methylresorcinol (HO—C₆H₃(CH₃)—OH) | | | X | | | | | | | | | | X | |
| 1-naphthol | | | | | X | | | | | | | | | X |
| 2-methyl-1-naphthol | | | | | X | | | | | | | | | |
| 2,4-diamino-1-(2-hydroxyethoxy)benzene | | | | | | X | | | | | | | | |
| 1,3-phenylenediamine | | | | | | | | X | | | | | | |
| 3-aminophenol | | | | | | | | | X | | | | | |
| 5-amino-2-methylphenol | | x | | | | | | | | X | | | | |
| 4,5-diamino-1-(2-hydroxyethyl)pyrazole | | | | | | | | | | | X | X | X | X |

DYE COMBINATIONS

TABLE A-continued

| Structure | | | | | | | | | | | | | |
|---|---|---|---|---|---|---|---|---|---|---|---|---|---|
| 4-amino-2-hydroxy with R³ and pyridinium-methylamino substituent | X | X | X | X | X | X | X | X | X | X | X | X | X |
| 2-methyl-1,4-phenylenediamine | | | X | X | X | X | X | | | | | | |
| 1,4-phenylenediamine | | | | | | | X | X | X | X | X | X | X | X | X |
| N,N-bis(2-hydroxyethyl)-1,4-phenylenediamine | | | | | | | | | | | | | |
| 4-aminophenol | | | | | | | | | | | | | |
| 4-amino-3-methylphenol | | | | | | | | | | | | | |
| 2-aminophenol | | | | | | | | | | X | | | |
| resorcinol | | | | | | | | | | | X | | |

TABLE A-continued
| Structure | C109 | C110 | C111 | C112 | C113 | C114 | C115 | C116 | C117 | C118 | C119 | C120 | C121 | C122 |
|---|---|---|---|---|---|---|---|---|---|---|---|---|---|---|
| 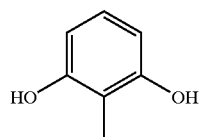 | | | | | | | X | | | | | | | |
| 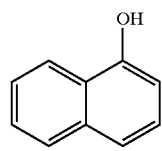 | | | | | | | | | X | | | | | |
| 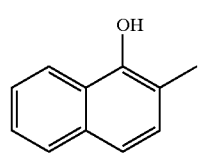 | | | X | | | | | | | X | | | | |
| 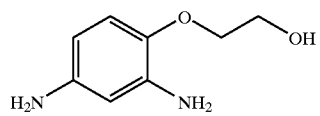 | | | | X | | | | | | X | | | | |
| 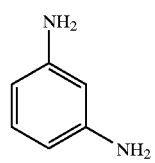 | | | | X | | | | | | X | | | | |
| 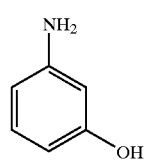 | | | | | X | | | | | | X | | | |
| 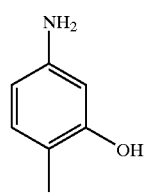 | | | | | | | X | | | | | | | X |
| 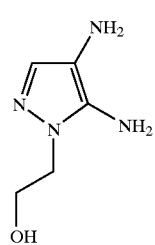 | X | X | X | X | X | X | X | X | X | X | X | X | X | X |
DYE COMBINATIONS TABLE A-continued
| Structure | | | | | | | | | | | | | |
|---|---|---|---|---|---|---|---|---|---|---|---|---|---|
| 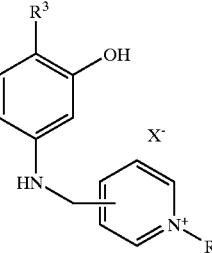 | X | X | X | X | X | X | X | X | X | X | X | X | X |
| 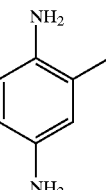 | | | | | | | | | | | | | |
| 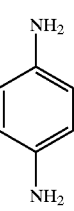 | | | | | | | | | | | | | |
| 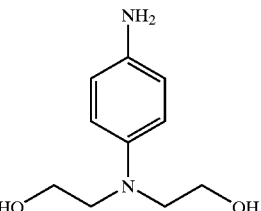 | | | | | | | | | | | | | |
| 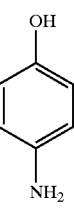 | X | X | X | X | X | X | X | X | X | | | | |
| 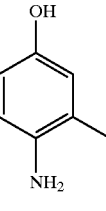 | | | | | | | | | | X | X | X | X | X |
| 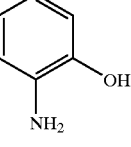 | | | | | | | | | | | | x | |
| 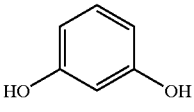 | | | | | | | | | | | | x | |

TABLE A-continued
| Structure | | | | | | | | | | | | | | |
|---|---|---|---|---|---|---|---|---|---|---|---|---|---|---|
| 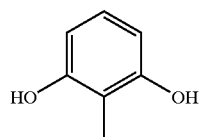 | | | | | | | | | | | | | | x |
| 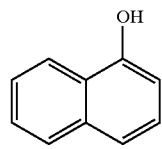 | | | | | | | | | | | | | | x |
| 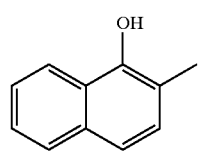 | | | | | | | | | | | | | | x |
| 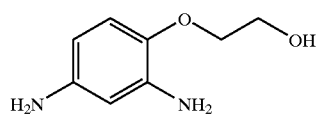 | | | | | | | | | | | | | | |
| 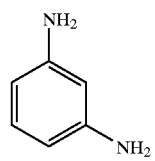 | | | | | | | | | | | | | | |
| 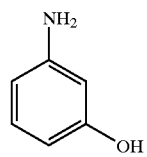 | | | | | | | | | | | | | | |
| 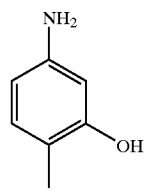 | | | | | | | | | | | | | | |
| 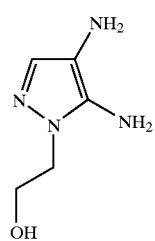 | x | x | x | x | x | x | x | x | x | x | x | x | x | x |
DYE COMBINATIONS
| Structure | C123 | C124 | C125 | C126 |
|---|---|---|---|---|

TABLE A-continued

| Structure | | | | |
|---|---|---|---|---|
| 4-(R³-substituted)-3-hydroxyphenyl aminomethyl pyridinium (R on N⁺), X⁻ | X | X | X | X |
| 2-methyl-1,4-diaminobenzene | | | | |
| 1,4-diaminobenzene | | | | |
| 4-amino-N,N-bis(2-hydroxyethyl)aniline | | | | |
| 4-aminophenol | | | | |
| 4-amino-3-methylphenol | X | X | X | x |
| 2-aminophenol | | | | |
| resorcinol | | | | |

TABLE A-continued

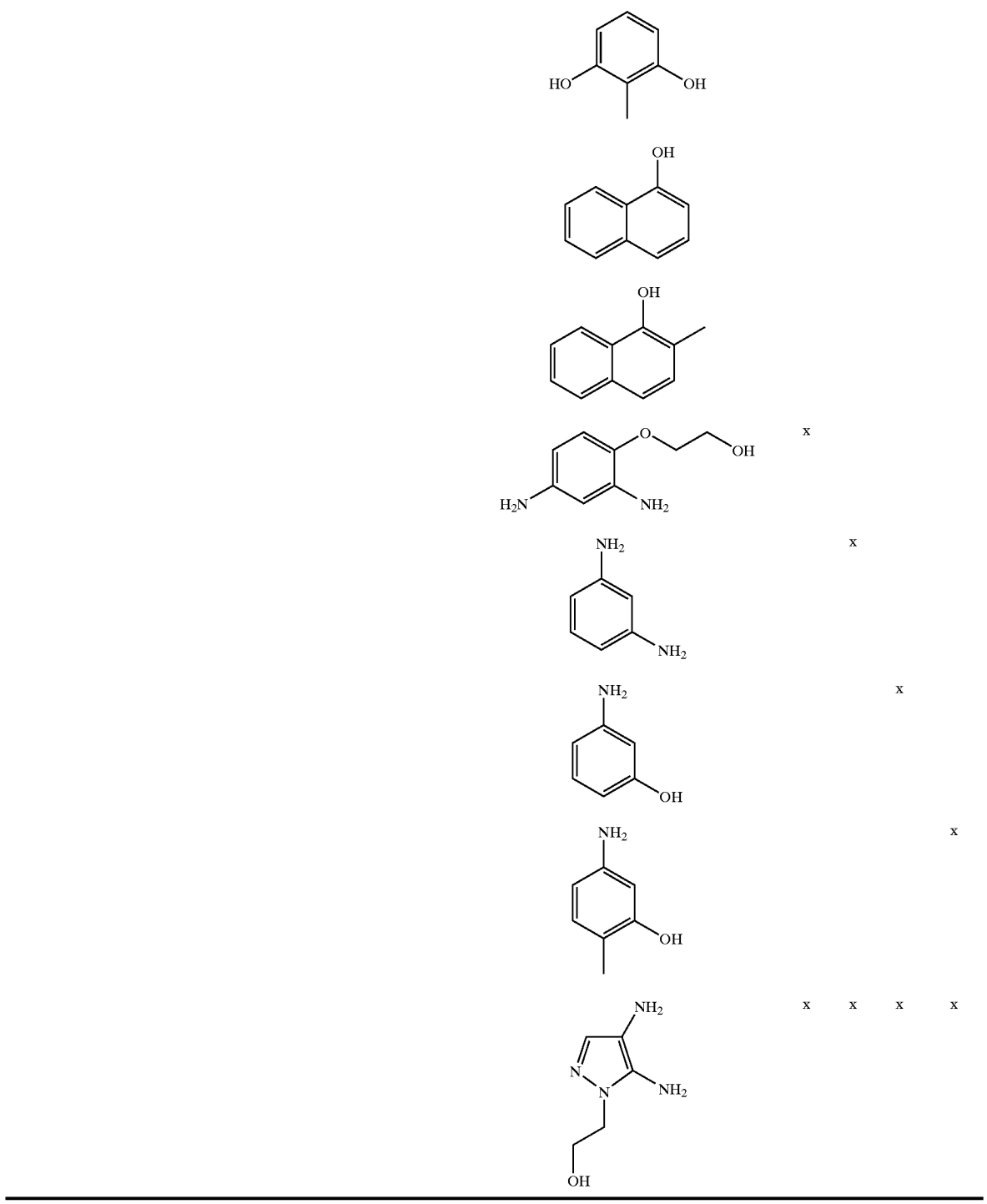

EXAMPLE 11

Piedmont hair weighing from 700 to 900 mg is used. The concentration of the primary intermediate and the coupler 7 is 0.025 M in the dye base. The dye base consists of cocamidopropyl betaine 17 g, monoethanol amine 2.0 g, oleic acid 0.75 g, citric acid 0.1 g, 28% ammonia 5.0 g, behentrimonium chloride 0.5 g, sodium sulfite 0.1 g, EDTA 0.1 g, erythorbic acid 0.4 g, ethoxydiglycol 3.5 g, C11–15 pareth-9 1.0 g, C12–15 pareth-3 0.5 g, isopropanol 4.0 g, propylene glycol 2.0 g and water to qs 100 g. The developer consists of 50% hydrogen peroxide 12.0 g, Aculyn-22 1.0 g, Aculyn-33 12.0 g, phosphoric acid to pH 3.0 and water to qs 100 g. A mixture of the primary intermediate solution (0.5 mL) and the coupler solution (0.5 mL) is mixed with the developer (1 mL). The mixture is applied to the hair tresses mounted on a glass plate and then stored at 40° C. for 30 min, washed, shampooed, rinsed and dried. Color is evaluated using the Minolta Spectrophotometer CM-3700d (Table 2).

TABLE 2

CIE L*a*b* values obtained from Compound 7 with various primary intermediates

| Compound 7 | PAP | | | PPD | | | PTD | | | Pyrazole | | |
|---|---|---|---|---|---|---|---|---|---|---|---|---|
| | L* | a* | b* | L* | a* | b* | L* | a* | b* | L* | a* | b* |
| R = Methyl | 59.44 | 12.80 | 21.55 | 40.49 | 12.40 | 0.71 | 44.41 | 9.48 | −2.51 | 46.52 | 33.48 | 22.77 |
| R = Ethyl | 61.36 | 14.23 | 22.26 | 40.37 | 12.95 | 0.71 | 48.15 | 8.46 | −0.04 | 44.47 | 29.64 | 20.07 |

PAP: 4-aminophenol,
PPD: p-phenylenediamine,
PTD: p-Toluenediamine,
Pyrazole: 1-(2-Hydroxyethyl)-4,5-diaminopyrazole With the foregoing description of the invention, those skilled in the art will appreciate that modifications may be made to the invention without departing from the spirit thereof. Therefore, it is not intended that the scope of the invention be limited to the specific embodiments illustrated and described.

We claim:

1. In a hair coloring system comprising a composition containing one or more oxidative hair coloring agents and a composition containing one or more oxidizing agents, the improvement comprising the presence in the composition containing one or more oxidative hair coloring agents of a coupler comprising a compound of formula (1):

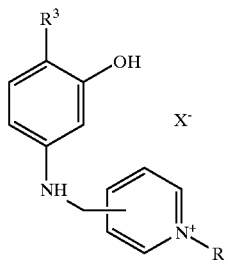

(1)

wherein X is selected from the group consisting of halogen and $R^2SO_4$; $R^3$ is selected from the group consisting of $C_1$ to $C_2$ alkyl or hydroxyethyl; $R^2$ is selected from the group consisting of $C_1$ to $C_{22}$ alkyl and $C_1$ to $C_{22}$ mono and dihydroxyalkyl; and R is selected from the group consisting of $C_1$ to $C_{16}$ alkyl, $C_1$ to $C_{10}$ hydroxyalkyl, $C_1$ to $C_6$ alkoxyalkyl and benzyl.

2. A hair coloring system according to claim 1 wherein the composition comprising one or more oxidative hair coloring agents additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine, 2-(4,5-diamino-1H-pyrazol-1-yl)ethanol, 1-(4-methylbenzyl)-1H-pyrazole-4,5-diamine, and 1-(benzyl)-1H-pyrazole-4,5-diamine.

3. A hair coloring system according to claim 1 wherein $R^3$ is a methyl group; R is selected from the group consisting of $C_1$ to $C_3$ alkyl, $C_1$ to $C_3$ hydroxyalkyl, $C_1$ to $C_4$ alkoxyalkyl and benzyl; and X is selected from Cl, Br, and $R^2SO_4$ where $R^2$ is $C_1$ to $C_3$ alkyl.

4. In a system for coloring hair wherein at least one primary intermediate is reacted with at least one coupler in the presence of an oxidizing agent to produce an oxidative hair dye, the improvement wherein the at least one coupler comprises a compound of the formula (1):

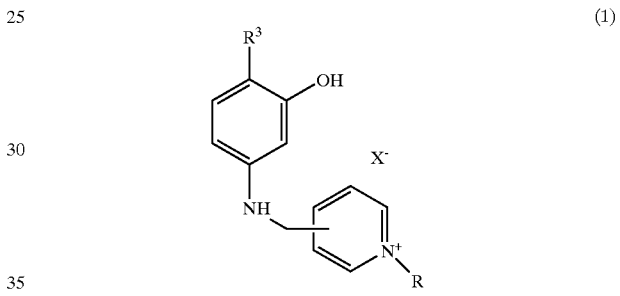

(1)

wherein X is selected from the group consisting of halogen and $R^2SO_4$; $R^3$ is selected from the group consisting of $C_1$ to $C_2$ alkyl or hydroxyethyl; $R^2$ is selected from the group consisting of $C_1$ to $C_{22}$ alkyl and $C_1$ to $C_{22}$ mono and dihydroxyalkyl; and R is selected from the group consisting of $C_1$ to $C_{16}$ alkyl, $C_1$ to $C_{10}$ hydroxyalkyl, $C_1$ to $C_6$ alkoxyalkyl and benzyl.

5. A system for coloring hair according to claim 4 wherein the system additionally comprises one or more primary intermediates selected from the group consisting of: 2-methyl-benzene-1,4-diamine, benzene-1,4-diamine, 2-(2,5-diamino-phenyl)-ethanol, 1-(2,5-diamino-phenyl)-ethanol, 2-[(4-amino-phenyl)-(2-hydroxy-ethyl)-amino]-ethanol, 4-amino-phenol, 4-methylamino-phenol, 4-amino-3-methyl-phenol, 1-(5-amino-2-hydroxy-phenyl)-ethane-1,2-diol, 2-amino-phenol, 2-amino-5-methyl-phenol, 2-amino-6-methyl-phenol, N-(4-amino-3-hydroxy-phenyl)-acetamide, pyrimidine-2,4,5,6-tetramine, 2-(4,5-diamino-1H-pyrazol-1-yl)ethanol, 1-(4-methylbenzyl)-1H-pyrazole-4,5-diamine, and 1-(benzyl)-1H-pyrazole-4,5-diamine.

6. A system for coloring hair according to claim 4 wherein the system contains one or more couplers selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

7. A system for coloring hair according to claim 5 wherein the system contains one or more couplers selected from the group consisting of: benzene-1,3-diol, 4-chlorobenzene-1,3-diol, naphthalen-1-ol, 2-methyl-naphthalen-1-ol, 2-methyl-benzene-1,3-diol, 2-(2,4-diamino-phenoxy)-ethanol, 2-(3-amino-4-methoxy-phenylamino)-ethanol, 2-[2,4-diamino-5-(2-hydroxy-ethoxy)-phenoxy]-ethanol, and 3-(2,4-diamino-phenoxy)-propan-1-ol, 3-amino-phenol, 5-amino-2-methyl-phenol, 5-(2-hydroxy-ethylamino)-2-methyl-phenol, 3-amino-2-methyl-phenol, 3,4-dihydro-2H-1,4-benzoxazin-6-ol, 4-methyl-2-phenyl-2,4-dihydro-3H-pyrazol-3-one, 1H-indol-6-ol, and 2-aminopyridin-3-ol.

8. A system for coloring hair according to claim 5 wherein $R^3$ is a methyl group; R is selected from the group consisting of $C_1$ to $C_3$ alkyl, $C_1$ to $C_3$ hydroxyalkyl, $C_1$ to $C_4$ alkoxyalkyl and benzyl; and X is selected from Cl, Br, and $R^2SO_4$ where $R^2$ is $C_1$ to $C_3$ alkyl.

9. A hair coloring composition for dyeing human hair comprising, in a suitable carrier or vehicle, a dyeing effective amount of:

(a) at least one primary intermediate, (b) at least one coupler comprising a compound of the formula (1):

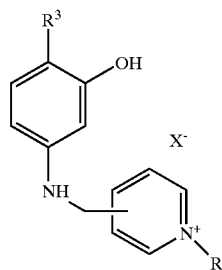

(1)

wherein X is selected from the group consisting of halogen and $R^2SO_4$; $R^3$ is selected from the group consisting of $C_1$ to $C_2$ alkyl or hydroxyethyl; $R^2$ is selected from the group consisting of $C_1$ to $C_{22}$ alkyl and $C_1$ to $C_{22}$ mono and dihydroxyalkyl; and R is selected from the group consisting of $C_1$ to $C_{16}$ alkyl, $C_1$ to $C_{10}$ hydroxyalkyl, $C_1$ to $C_6$ alkoxyalkyl and benzyl; and (c) at least one oxidizing agent.

10. A hair coloring composition of claim 8 wherein $R^3$ is a methyl group; R is selected from the group consisting of $C_1$ to $C_3$ alkyl, $C_1$ to $C_3$ hydroxyalkyl, $C_1$ to $C_4$ alkoxyalkyl and benzyl; and X is selected from Cl, Br, and $R^2SO_4$ where $R^2$ is $C_1$ to $C_3$ alkyl.

11. A process for dyeing human hair comprising applying a dyeing effective amount of a hair coloring composition of claim 7 to the hair and permitting the composition to contact the hair for a dyeing effective period of time, and then rinsing, shampooing and drying the hair.

12. A process according to claim 9 wherein $R^3$ is a methyl group; R is selected from the group consisting of $C_1$ to $C_3$ alkyl, $C_1$ to $C_3$ hydroxyalkyl, $C_1$ to $C_4$ alkoxyalkyl and benzyl; and X is selected from Cl, Br, and $R^2SO_4$ where $R^2$ is $C_1$ to $C_3$ alkyl.

* * * * *